United States Patent [19]

An-hsiang

[11] Patent Number: 5,166,114
[45] Date of Patent: Nov. 24, 1992

[54] ETHYLENE DIMERIZATION AND CATALYST THEREFOR

[75] Inventor: Wu An-hsiang, Bartlesville, Okla.

[73] Assignee: Phillips Petroleum Company, Bartlesville, Okla.

[21] Appl. No.: 820,433

[22] Filed: Jan. 14, 1992

[51] Int. Cl.$^5$ .............................. B01J 31/08
[52] U.S. Cl. .................... 502/117; 502/159
[58] Field of Search .................. 502/117, 159

[56] References Cited

U.S. PATENT DOCUMENTS

| | | | |
|---|---|---|---|
| 3,452,115 | 6/1969 | Schneider | 260/683.15 |
| 3,513,218 | 5/1970 | Faltings et al. | 260/683.15 |
| 4,038,213 | 7/1977 | McClure et al. | 252/430 |
| 4,179,402 | 12/1979 | Kim et al. | 585/277 |
| 4,189,403 | 2/1980 | Roobeek | 252/431 |
| 4,528,415 | 7/1985 | Knudsen | 585/527 |

Primary Examiner—Patrick P. Garvin
Assistant Examiner—Brent M. Peebles
Attorney, Agent, or Firm—Lucas K. Shay

[57] ABSTRACT

An ethylene dimerization process catalyzed by a heterogeneous catalyst comprising a nickel compound, a phosphine compound, an organoaluminum compound, and a perfluorosulfonate polymer is provided. The dimerization process comprises contacting ethylene under dimerization conditions with the catalyst which is prepared by adding a homogeneous solution, formed by mixing under ethylene pressure the organoaluminum solution with a mixture of the nickel compound and the phosphine compound, to a suspension of the perfluorosulfonate polymer in an alcohol.

15 Claims, No Drawings

ETHYLENE DIMERIZATION AND CATALYST THEREFOR

FIELD OF THE INVENTION

The invention relates to a process for the dimerization of ethylene to butenes and a catalyst for the dimerization process. It also relates to a process for preparing the catalyst.

BACKGROUND OF THE INVENTION

Many catalysts containing a nickel compound are known to dimerize ethylene to butenes. For example, U.S. Pat. No. 4,528,415 discloses a process for the dimerization of ethylene using a catalyst consisting essentially of a nickel(O) complex, a phosphine compound, and an acid; U.S. Pat. No. 3,513,218 discloses an olefin dimerization process employing a catalyst comprising a nickel(II) compound, an electron donor, and an organoaluminum halide; U.S. Pat. No. 3,452,115 discloses an olefin dimerization process catalyzed by a catalyst consisting of a nickel(II) compound mixed with an alkylaluminum and a halide.

However, by using the above-referenced processes employing the catalysts disclosed, one has not always achieved high catalyst productivity, good product selectivity, or both. Additionally, some known processes require long reaction time, high temperature, or both to convert ethylene to butenes.

Because of the increasing importance of 1-butene as industrial feedstock, processes and catalysts that make even slight improvements in the availability of 1-butene over the known processes and catalysts are highly desirable.

SUMMARY OF THE INVENTION

It is, therefore, an object of the invention to provide an improved catalyst for the dimerization of ethylene. It is also an object of the invention to provide a process for preparing the catalyst. A further object of the invention is to provide a process for the dimerization of ethylene using the catalyst at lower temperature. Another object of the invention is to provide a process to prepare 1-butene with high selectivity from ethylene by dimerization process of ethylene. Yet still a further object of the invention is to provide a dimerization process that has an advantage of preparing 1-butene, using the inventive catalyst, by decreasing the reaction temperature. Other aspects, objects, advantages and features of the invention will become apparent from the specification and claims.

According to the first embodiment of the invention, a catalyst useful for the dimerization of ethylene is provided which comprises a nickel compound, an organoaluminum compound, a phosphine compound, and a perfluorosulfonate polymer.

According to the second embodiment of the invention, a process for dimerization of ethylene catalyzed by a catalyst comprising a nickel compound, an organoaluminum compound, a phosphine compound, and a perfluorosulfonate polymer is provided which comprises: (1) combining a mixture of the nickel compound and the phosphine compound in a hydrocarbon solvent and the organoaluminum compound under ethylene pressure to form the mixture to form a homogeneous solution; (2) adding the homogeneous solution to a suspension of the perfluorosulfonate polymer in a second solvent to form a heterogeneous catalyst system; (3) contacting ethylene with the catalyst system under dimerization conditions to produce butenes; and (4) recovering the butenes.

DERAILED DESCRIPTION OF THE INVENTION

The first embodiment of the invention relates to a catalyst system useful for ethylene dimerization comprising a nickel compound, an organoaluminum compound, a phosphine compound, and a perfluorosulfonate polymer.

The nickel compound has a nickel atom bonded to at least one organic moiety and has an oxidation state of 2. The preferred nickel compound is selected from the group consisting of bis(cyclopentadienyl) nickel(II), bis(pentamenthylcyclopentadienyl) nickel(II), nickel(II) 2-ethylhexanoate, nickel(II) acetylacetonate, nickel(II) trifluoroacetylacetonate, nickel(II) hexafluoroacetylacetonate, nickel(II) acetate, nickel(II) hydroxyacetate, nickel(II) stearate, nickel(II) tetrafluoroborate, nickel(II) cyclohexylbutyrate and nickel(II) oxalate. The first six listed oganonickel(II) compounds, particularly nickel(II) acetylacetonate, are more preferred. In addition, a hydrated form of the nickel compound is most preferred as being less expensive and more stable than the anhydrous form of such compound, although anhydrous form can be employed if desired.

The phosphine compound has the formula of $PR_3$, where R independently represents H or a $C_1$ to $C_{20}$ hydrocarbyl radical and where at least one R is not H. Suitable phosphine compounds include cyclohexylphosphine, dicyclohexylphosphine, tricyclohexylphosphine, triethylphosphine, triisopropylphosphine, triisobutylphosphine, tri-n-butylphosphine, tri-t-butylphosphine, diphenylphosphine, triphenylphosphine, diphenylcyclohexylphosphine, diethylphenylphosphine, ortho-tolydiphenylphosphine, di(ortho-tolyl)phenylphosphine and tribenzylphosphine. Tricyclohexylphosphine and triisopropylphosphine are preferred.

Suitable organoaluminum compounds are those having at least one $C_1$ to $C_{12}$, preferably $C_1$ to $C_6$, alkyl radical and at least one aluminum atom per molecule, and include triisobutylaluminum, triethylaluminum, trimethylaluminum, di-isobutylaluminum chloride, diisobutylaluminum hydride, diethylaluminum chloride and triethyldialuminum trichloride. Particularly preferred in accordance with the invention is a trialkylaluminum compound of the formula $AlR'_3$ where R' is the above-mentioned alkyl radical, such as triisobutylaluminum, triethylaluminum or trimethylaluminum. Triethylaluminum is most preferred.

The perfluorosulfonate polymer useful in this invention is a copolymer of a perfluorovinyl ether having a sulfonic acid group and a fluorocarbon such as perfluoroethylene, has a maximum equivalent weight of about 1250, and has the following formula:

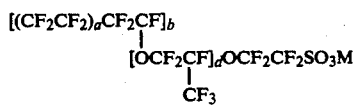

where a and d are integers and are $\geq 1$, b represents repeating units and M is an alkali metal. The polymer is commercially available as a membrane 5 to 10 mils thick, or in pellet, or bead, or powder form. The physical form of the polymer is a mater of chloride for one skilled in the art. All forms will provide the catalyst effect of the invention. A further description of the perfluorosulfonate polymer is given in U.S. Pat. No. 4,038,213 which is incorporate herein by reference. Preferred perfluorosulfonate polymer is Nafion ®NR50 (10-35 mesh) with maximum equivalent weight of 1250.

The molar ratio of the phosphine compound to the nickel compound suitable for the invention is generally about 0.1 to about 2, preferably about 0.5 to about 1.5, and most preferably 0.8 to 1.2. The suitable molar ratio of the organoaluminum compound to the nickel compound is about 1 to about 5, preferably about 1.5 to about 3, and most preferably 1.8 to 2.5. The molar ratio of the perfluorosulfonate polymers to the nickel compound is about 0.001 to about 1000, preferably about 0.1 to about 10, and most preferably 0.3 to 1.

The catalyst system can be generally prepared by first forming a mixture of the nickel compound and the phosphine compound in a hydrocarbon solvent at about 0° C. to about 100° C., preferably at ambient temperature, under ethylene atmosphere. The ethylene pressure is about 10 psig to about 100 psig, preferably about 15 psig to about 30 psig. The preferred solvent is a hydrocarbon and the most preferred is an aromatic hydrocarbon. The suitable aromatic hydrocarbon includes benzene, toluene, p-xylene, o-xylene, m-xylene, ethylbenzene, propylbenze, p-ethytoluene, styrene, phenylacetylene, and other aromatic hydrocarbons. The presently preferred hydrocarbon is toluene.

A solution of the organoaluminum compound under ethylene atmosphere (about 40 to 100 psig) and at about 0° C. to about 100° C., preferably ambient temperature is then combined to the above mixture to form a homogeneous solution. The reaction time for forming the solution is generally about 30 minutes to 2 hours depending on the concentrations of the components.

Finally, the homogeneous solution is added to a suspension of a perfluorosulfonate polymer, preferably an activated perfluorosulfonate polymer, in a second solvent, preferably an aliphatic alcohol, under ethylene pressure (from about 50 to 200 psig) and at about 0° C. to about 100° C., preferably at ambient temperature, to form a heterogeneous catalyst. The activation of a perfluorosulfonate polymers is simply an acidification to convert the polymer from a salt form to a free acid form. The acidification can be carried out by any suitable means, such as using a hydrochloric acid solution. Preferred aliphatic alcohol is saturated and has 1 to 15 carbon atoms. Presently most preferred saturated aliphatic alcohol has 6 to 10 carbon atoms, such as 1-octanol.

According to the second embodiment of the invention, a process for ethylene dimerization is provided. In the first step of the dimerization process, a mixture of the nickel compound and the phosphine compound is formed in hydrocarbon solvent at about 0° C. to about 100°C., preferably at ambient temperature, under ethylene atmosphere. The ethylene pressure is about 15 psig to about 100 psig, preferably about 15 psig to about 30 psig. The preferred solvent is an aromatic hydrocarbon. The suitable aromatic hydrocarbon includes benzene, toluene, p-xylene, o-xylene, m-xylene, ethylbenzene, propylbenze, p-ethytoluene, styrene, phenylacetylene, and other aromatic hydrocarbons. The presently preferred hydrocarbon is toluene.

The nickel compound has a nickel atom bonded to at least one organic moiety and has an oxidation state of 2. The preferred nickel compound is selected from the group consisting of bis(cyclopentadienyl) nickel(II), bis(pentamenthylcyclopentadienyl) nickel(II), nickel(II) 2-ethylhexanoate, nickel(II) acetylacetonate, nickel(II) trifluoroacetylacetonate, nickel(II) hexafluoroacetylacetonate, nickel(II) acetate, nickel(II) hydroxyacetate, nickel(II) stearate, nickel(II)tetrafluoroborate, nickel(II) cyclohexylbutyrate and nickel(II) oxalate. The first six listed oganonickel(II) compounds, particularly nickel(II) acetylacetonate, are more preferred. In addition, a hydrated form of the nickel compound is most preferred as being less expensive and more stable than the anhydrous form of such compound, although anhydrous form can be employed if desired.

The phosphine compound has the formula of $PR_3$, where R independently represents H or a $C_1$ to $C_{20}$ hydrocarbyl radical and where at least one R is not H. Suitable phosphine compounds include cyclohexylphosphine, dicyclohexylphosphine, tricyclohexylphosphine, triethylphosphine, triisopropylphosphine, triisobutylphosphine, tri-n-butylphosphine, tri-t-butylphosphine, diphenylphosphine, triphenylphosphine, diphenylcyclohexylphosphine, diethylphenylphosphine, ortho-tolydiphenylphosphine, di(ortho-tolyl)phenyl phosphine and tribenzylphosphine. Tricyclohexylphosphine and triisopropylphosphine are preferred as giving the optimum distribution of oligomers in the $C_4$–$C_{10}$ range.

In the second step, a solution of the organoaluminum compound under ethylene atmosphere (about 40 to about 100 psig; preferably about 50 to about 70 psig) and at about 0° C. to about 100° C., preferably at ambient temperature is then added to the above mixture under the same conditions described above to form a homogeneous solution. The reaction time for forming the solution is generally about 30 minutes to 2 hours depending on the concentrations of the components.

Suitable organoaluminum compounds are those having at least one $C_1$ to $C_{12}$, preferably $C_1$ to $C_6$, alkyl radical and at least one aluminum atom per molecule, include triisobutylaluminum, triethylaluminum, trimethylaluminum, di-isobutylaluminum chloride, diisobutylaluminum hydride, diethylaluminum chloride and triethyldialuminum trichloride. Particularly preferred in accordance with the invention is a trialkylaluminum compound of the formula $AlR'_3$ where R' is the above-mentioned alkyl radical, such as triisobutylaluminum, triethylaluminum or trimethylaluminum. Triethylaluminum is most preferred.

In the third step, an activated perfluorosulfonate polymer in an aliphatic alcohol, under ethylene pressure (from about 50 to 200 psig) and at about 0° C. to about 100° C., preferably at ambient temperature is then added to the above solution to form a heterogeneous catalyst. The activation of a perfluorosulfonate polymers is simply an acidification to convert the polymer from a salt form to a free acid form. The acidification can be carried out by any suitable means, such as using a hydrochloric acid solution. Preferred aliphatic alcohol is saturated and has 1 to 15 carbon atoms. Presently most preferred saturated aliphatic alcohol has 6 to 10 carbon atoms, such as 1-octanol.

The perfluorosulfonate·polymer useful in this invention is a copolymer of a perfluorovinyl ether having a sulfonic acid group and a fluorocarbon such as perfluoroethylene, has a maximum equivalent weight of about 1250, and has the following formula:

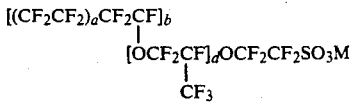

where a and d are integers and are ≧1, b represents repeating units and M is a metal, preferably an alkali metal. The polymer is commercially available as a membrane 5 to 10 mils thick, or in pellet, or bead, or powder form. The physical form of the polymer is a mater of chloride for one skilled in the art. All forms will provide the catalyst effect of the invention. A further description of the perfluorosulfonate polymer is given in U.S. Pat. No. 4,038,213 which is incorporate herein by reference. Preferred perfluorosulfonate polymer is Nafion®NR50 (10-35 mesh) with maximum equivalent weight of 1250.

The molar ratio of the phosphine compound to the nickel compound suitable for the invention is about 0.1 to about 2, preferably about 0.5 to about 1.5, and most preferably 0.8 to 1.2. The suitable molar ratio of the organoaluminum compound to the nickel compound is about 1 to about 5, preferably about 1.5 to about 3, and most preferably 1.8 to 2.5. The molar ratio of the perfluorosulfonate polymers to the nickel compound is about 0.001 to about 1000, preferably about 0.1 to about 10, and most preferably 0.3 to 1.

The next step involves the contacting of ethylene with the heterogeneous catalyst under dimerization conditions to produce butenes. The ethylene can be applied to the catalyst system at about 100 psig to about 5000 psig, preferably about 200 psig to about 1500 psig. The most preferred pressure ranges from about 500 psig to about 1000 psig. The reaction temperature is about 0° C. to about 125° C., preferably about 20° C. to about 60° C. With respect to time, it is preferred to carry out for about 1 minute to about 6 hour, most preferably about 15 minutes to about 3 hours.

Finally, the dimerization products as contained in the reaction mixture can be separated and recovered from the catalyst by conventional means such as fractionation distillation.

Any appropriate vessels that can be pressurized and maintain high pressure to 5000 psig can be used in the dimerization process of the invention. Preferred vessels are stainless steel reactors equipped with inlet valves for pressurizing the vessel with ethylene, which is also serves as the reactant, for addition of the catalyst components, and for discharging the catalyst components as well as reaction mixture; agitation means such as power agitator for mixing; temperature control means such as a jacket or inner heat exchangers; and other optional equipment. The type of vessels is a matter of choice for one skilled in the art.

EXAMPLES

Examples are set forth below which further illustrate the invention but which should not be construed to limit the invention in any manner.

Each example employed at least one 300 mL stainless steel (316SS) Autoclave Engineers stirred tank autoclave, hereafter denoted simply as a reactor. Other equipment employed in individual examples will be referenced in those examples. It is understood that the contents of such reactor(s) in the following examples are being agitated, typically at a slow agitation of about 300 rpm during purging of the reactor or addition of various reagents to the reactor, and at a normal agitation of about 1600 rpm at all other times.

Product analysis was performed on approximately 5 gram samples with an HP 5890 II GC-FID Spectrometer equipped with a capillary DB-1 (60 m) column. The column was operated at 30° C. for 5 minutes, followed by a 15° C./minute increase to 285° C. which was held for 13 minutes. Detection was obtained using a flame ionization detector in the area percent mode. Selectivity and weight percent distribution, discussed further below, were determined from spectra as recorded by the spectrometer.

In the following examples, results are reported items of productivity, selectivity to 1-butene and wight percent distribution of butenes. Productivity is defined as the grams of dimerization product produced per gram of the nickel compound per hour, and was calculated in each example based on grams of ethylene reacted. Selectivity to 1-butene is given in terms of the weight percent of total butenes produced. The distribution of the butenes is given as the weight percent of 1-butene, trans-2-butene and cis-2-butene.

EXAMPLE I

This example illustrates the dimerization process of the invention using the inventive catalyst system with tricyclohexylphosphine as the phosphine component.

In a 300 mL stainless steel reactor equipped with an addition value which was connected with an addition sample vessel. The reactor was purged with nitrogen for 5 minutes followed by addition of 1.39 g (4.75 mmol) of nickel acetylacetonate hydrate, 1.33 g (4.75 mmol) tricyclohexylphosphine and 45 mL of freshly distilled toluene. The reactor was then sealed, purged with ethylene at least 5 times and pressurized with ethylene to 20 psig followed by agitation for 5 minutes. This reactor was labeled reactor 1.

A solution of triethylaluminum (1.9 M; 5.0 mL; 9.5 mmol) under 50 psig ethylene pressure in a 40 mL additional vessel, equipped with an outlet into the above reactor 1, was added to the reactor 1 through the addition valve. The pressure of the reactor 1 was maintained at 50 psig with ethylene for 60 minutes whereby a homogeneous solution was formed.

A separate sealed reactor, equipped the same as the one described above, labeled reactor 2, was used for the dimerization process. Following at least 3 time ethylene purges, agitated Nafion®NR50, a perfluorosulfonate polymer, (0.5 g; 0.4 mmol; commercially available from Aldrich Chemical Co.) and 35 mL of 1-octanol were added to reactor 2. Activation of Nafion®NR50 was carried out by treating Nafion®NR50 with 10 weight % HCl solution for 30 minutes followed by drying under reduced pressure (200° C., 1 mmHg) for 24 hours. Five milliliters of the homogeneous solution prepared in reactor 1 was then added to reactor 2 using a pressure-resistant burette through the addition valve of reactor 2 while agitating. Upon completion of the addition, reactor 2 was pressurized to 700 psig with ethylene and maintained at 700 psig for 1 hour at a temperature indicated in Table I below. The product was analyzed and the results are shown in Table I.

TABLE I

Ethylene Dimerization With a Catalyst Comprising Nafion-H

| Run No. | Temp. (°C.) | Productivity[a] | Selectivity (%)[b] | Product Distribution (wt. %) | |
|---|---|---|---|---|---|
| | | | | Butenes | Higher[c] |
| 1 | 100 | 1483 | 90 | 86 | 14 |
| 2 | 80 | 1850 | 92 | 87 | 13 |
| 3 | 70 | 2062 | 94 | 90 | 10 |
| 4 | 60 | 2166 | 96 | 92 | 8 |
| 5 | 50 | 2281 | 97 | 94 | 6 |
| 6 | 40 | 2360 | 97 | 98 | 2 |

[a]Productivity is expressed as g butenes/g nickel compound/hour.
[b]1-Butene.
[c]Higher denotes to hexenes and trace of octenes.

The results shown in Table I clearly indicate that the inventive catalyst has very high activity, up to 2360 g/g/hr at low temperature (run 6). Furthermore, majority of the product was butenes (98%), of which 97% was 1-butene (run 6). However, as the reaction temperature was increased, the productivity, selectivity and weight percent of butenes decreased.

EXAMPLE II

This example illustrates that another phosphine compound, triisopropyl phosphine, when used as a component of the inventive catalyst, has even higher catalytic activity than that shown in Example I.

The runs were carried out exactly the same as those illustrated in Example I with the exception that triisopropyl phosphine was used to replace tricyclohexyl phosphine. The results are shown in Table II.

TABLE II

Ethylene Dimerization with a Catalyst Comprising Nafion-H

| Run No. | Reaction temp. (°C.) | Productivity[a] | Selectivity (%)[b] | Product distribution (wt %) | |
|---|---|---|---|---|---|
| | | | | Butenes | Higher[c] |
| 7 | 100 | 2482 | 91 | 87 | 13 |
| 8 | 80 | 2765 | 92 | 89 | 11 |
| 9 | 70 | 2958 | 94 | 90 | 10 |
| 10 | 60 | 3241 | 96 | 92 | 8 |
| 11 | 50 | 3354 | 98 | 95 | 5 |
| 12 | 40 | 3490 | 99 | 98 | 2 |

[a]Productivity is expressed as g butenes/g nickel compound/hr
[b]Selectivity to 1-butene
[c]Higher denotes to hexenes and trace amount of octenes Table II shows that, when isopropyl phosphine was used as a catalyst component, the catalyst activity increased, compared to Table I, to as high as 3490 g/g/hr (run 12). Similar to Table I, Table II demonstrates that the productivity, selectivity and weight % of butenes decreased with increased reaction temperature. It is concluded from the results of Table I and II the inventive catalyst and dimerization process produce high concentration of butenes with high selectivity to 1-butene at low temperatures.

EXAMPLE III

This example illustrates that the perfluorosulfonate polymer is a required component for the catalytic activity and no dimerization occurs in the absence of the polymer.

The runs were carried out the same as those shown in Example I, except that the activated Nafio-H was absent from the reactor 2. No dimerization reaction was detected for as long as 5 hours reaction time at 40° C.

That which is claimed is:

1. A catalyst comprising a nickel compound, an organoaluminum compound, an organic phosphine compound, and a perfluorosulfonate polymer.

2. A catalyst according to claim 1 wherein said nickel compound is selected from the group consisting of bis(cyclopentadienyl) nickel(II), bis(pentamenthylcyclopentadienyl) nickel(II), nickel(II) 2-ethylhexanoate, nickel(II) acetylacetonate, nickel(II) trifluoroacetylacetonate, nickel(II) hexafluoroacetylacetonate, nickel(II) acetate, nickel(II) hydroxyacetate, nickel(II) stearate, nickel(II)tetrafluoroborate, nickel(II) cyclohexylbutyrate and nickel(II) oxalate and hydrates thereof.

3. A catalyst according to claim 2 wherein said nickel compound is nickel(II) acetylacetonate.

4. A catalyst according to claim 2 wherein said nickel compound is nickel(II) acetylacetonate hydrate.

5. A catalyst according to claim 1 wherein said phosphine compound has the formula of $PR_3$, where R independently represents H or a $C_1$ to $C_{20}$ hydrocarbyl radical and where at least one R is not H.

6. A catalyst according to claim 5 wherein said phosphine compound is selected from the group consisting of cyclohexylphosphine, dicyclohexylphosphine, tricyclohexylphosphine, triethylphosphine, triisopropylphosphine, triisobutylphosphine, tri-n-butylphosphine, tri-t-butylphosphine, diphenylphosphine, triphenylphosphine, diphenylcyclohexylphosphine, diethylphenylphosphine, ortho-tolydiphenylphosphine, di(ortho-tolyl)phenylphosphine and tribenzylphosphine.

7. A catalyst according to claim 6 wherein said phosphine compound is a tricyclohexyl phosphine.

8. A catalyst according to claim 6 wherein said phosphine compound is triisopropyl phosphine.

9. A catalyst according to claim 1 wherein said organoaluminum compound has at least one $C_1$ to $C_{12}$ alkyl radical and at least one aluminum atom per molecule.

10. A catalyst according to claim 9 wherein said organoaluminum compound is selected from the group consisting of triisobutylaluminum, triethylaluminum, trimethylaluminum, di-isobutylaluminum chloride, diisobutylaluminum hydride, diethylaluminum chloride and triethyldialuminum trichloride.

11. A catalyst according to claim 10 wherein said organoaluminum compound is triethylaluminum.

12. A catalyst according to claim 1 wherein said perfluorosulfonate polymer is a copolymer of a perfluorovinyl ether having a sulfonic acid group and a fluorocarbon and has the following formula:

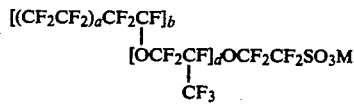

wherein a and d are integers and are $\geq 1$, b represents repeating units and M is an alkali metal.

13. A catalyst according to claim 12 wherein said perfluorosulfonate polymer is Nafion ®NR50 polymer.

14. A catalyst according to claim 1 wherein: said nickel compound is selected from the group consisting of bis(cyclopentadienyl) nickel(II), bis(pentamenthylcyclopentadienyl) nickel(II), nickel(II) 2-ethylhexanoate, nickel(II) acetylacetonate, nickel(II) trifluoroacetylacetonate, nickel(II) hexafluoroacetylacetonate, nickel(II) acetate, nickel(II) hydroxyacetate, nickel(II) stearate, nickel(II) tetrafluoroborate, nickel(II) cyclohexylbutyrate and nickel(II) oxalate and hydrates thereof; said phosphine compound is selected from the group consisting of cyclohexylphosphine, dicyclohexylphosphine, tricyclohexylphosphine, triethylphosphine, triisopropylphosphine, triisobutylphosphine, tri-n-butylphosphine, tri-t-butylphosphine, diphenylphosphine, triphenylphosphine, diphenylcyclohexylphosphine, diethylphenylphosphine, ortho-tolydiphenylphosphine, di(ortho-tolyl)phenylphosphine and tribenzylphosphine; said organoaluminum compound is selected from the group consisting of triisobutylaluminum, triethylaluminum, trimethylaluminum, diisobutylaluminum chloride, diisobutylaluminum hydride, diethylaluminum chloride and triethyldialuminum trichloride; and said perfluorosulfonate polymer is a copolymer of a perfluorovinyl ether having a sulfonic acid group and a fluorocarbon and has the following formula:

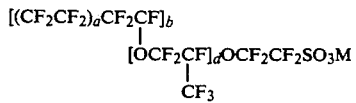

wherein a and d are integers and are $\geq 1$, b represents repeating units and M is an alkali metal.

15. A catalyst according to claim 14 wherein said nickel compound is nickel acetylacetonate hexahydrate; said phosphine compound is triisopropylphosphine; said organoaluminum compound is triethylaluminum; and said perfluorosulfonate polymer is Nafion ®NR50.

* * * * *

UNITED STATES PATENT AND TRADEMARK OFFICE
CERTIFICATE OF CORRECTION

PATENT NO. : 5,166,114
DATED : Nov. 24, 1992
INVENTOR(S) : An-hsiang Wu

It is certified that error appears in the above-identified patent and that said Letters Patent is hereby corrected as shown below:

On title page, item [75] Inventor: delete "Wu An-Hsiang"

should read --An-hsiang Wu--.

Signed and Sealed this

Fifth Day of October, 1993

Attest:

BRUCE LEHMAN

Attesting Officer

Commissioner of Patents and Trademarks